United States Patent [19]

McKee, Jr.

[11] Patent Number: 4,843,325
[45] Date of Patent: Jun. 27, 1989

[54] COMPLEMENTARY SENSING DEVICE FOR MINIMIZING THE EFFECTS OF COMMON MODE VOLTAGES

[75] Inventor: Charles B. McKee, Jr., Fort Collins, Colo.

[73] Assignee: In-Situ, Inc., Laramie, Wyo.

[21] Appl. No.: 150,017

[22] Filed: Jan. 29, 1988

[51] Int. Cl.⁴ ............................................. G01N 27/02
[52] U.S. Cl. .................... 324/439; 324/442; 330/258
[58] Field of Search ............... 324/441, 442, 443, 439, 324/444; 73/716, 717, 719, 725; 330/258

[56] References Cited

U.S. PATENT DOCUMENTS

| | | | |
|---|---|---|---|
| 4,118,663 | 10/1978 | Barben, II | 324/439 |
| 4,490,686 | 12/1984 | Dimett | 330/258 |
| 4,491,798 | 1/1985 | Palmer et al. | 324/442 |
| 4,595,884 | 6/1986 | Miller, Jr. | 330/258 |

FOREIGN PATENT DOCUMENTS 2753842  5/1979  Austria ................. 324/443

Primary Examiner—Reinhard J. Eisenzopf
Assistant Examiner—Maura K. Regan
Attorney, Agent, or Firm—Sheridan, Ross & McIntosh

[57] ABSTRACT

An apparatus and method are provided for reducing the effects that common mode currents and/or voltages have on the measurements made by instrumentation that senses physical phenomena. The apparatus includes a cell having a first sensor, a second sensor and a passageway for containing the fluid to be measured. The cell, sensors and passageway are symmetrically disposed about an axis. Due to this symmetry, a ground can be located at the axis of symmetry. The apparatus also includes first and second measuring circuits associated, respectively, with the first and second sensors. The first measuring circuit produces a signal respresentative of the measured parameter between the ground and the first sensor. The second measuring circuit provides a like function for the second sensor. The signals produced by the first and second measuring circuits are summed by a potentiometer. If a common mode voltage or current is present, it enters the circuitry through the ground located at the axis of symmetry and affects the signals generated by both the first and second measuring circuits. Due to the complementary nature of the apparatus, the common mode signal affecting the first measuring circuit is of an opposite polarity from that affecting the second measuring circuit. Due to this opposite polarity, the common mode signal can be reduced when the signals are summed at the potentiometer.

24 Claims, 3 Drawing Sheets

COMPLEMENTARY SENSING DEVICE FOR MINIMIZING THE EFFECTS OF COMMON MODE VOLTAGES

FIELD OF THE INVENTION

The present invention relates to a complementary sensing device for minimizing the effects of common mode voltages and currents which are detrimental to a measurement system's performance and present a safety hazard to personnel.

BACKGROUND OF THE INVENTION

Common mode voltages, also known as ground loop voltages, occur when the ground potential at one point in a circuit is different than the ground potential at another point in the circuit. In addition, if there is a finite resistance between the two ground points then a common mode current, also known as a ground loop current, flows in the circuit. When common mode currents exist in a circuit, they are generally detrimental to system performance and can present a safety hazard to personnel.

Prior art sensing circuitry included a sensor for detecting the presence of some physical phenomena, such as temperature or pressure, and generating an electrical signal representative of the sensed phenomena. The signal representative of the sensed phenomena was then transmitted to a processing station, also a part of the sensing circuitry, for analysis. Typically, the sensor would be located in close proximity, for example, to a grounded piece of equipment or power line, which would induce a common mode voltage in the sensing circuitry. If there was a finite resistance between, for example, the equipment ground and the sensing circuit ground, a common mode current would flow into the sensing circuitry thereby distorting the signal representative of the sensed phenomena. One way in which the prior art sought to prevent common mode currents was by introducing isolation circuitry between the sensor and the processing station to increase the impedance through the sensing circuitry. However, complete isolation is not possible and there is always some common mode current flow into the sensing circuitry due to capacitive coupling across the isolation barrier. Consequently, even if the common mode current is reduced by the power and isolation circuitry to the point where it does not present a safety hazard, it may still be significant with respect to, and thereby distort, the signals produced by the measurement instruments.

Exemplary of prior art sensors is U.S. Pat. No. 4,118,663 to Barben for a Four Electrode Conductivity Sensor. The sensor includes a conductivity cell having a passageway and a first and second pair of electrodes. The passageway contains a sample of the fluid whose conductivity is to be determined. One electrode of each pair of electrodes provides a feedback signal to a drive circuit which maintains the other electrode of the pair at a defined potential. Consequently, there are first and second drive circuits. The first drive circuit maintains a potential of V, generally an alternating potential to prevent polarization of the electrodes, at the location of the first pair of electrodes. The second drive circuit, on the other hand, maintains a ground potential at the location of the second pair of electrodes. The current necessary to maintain the defined potential at the location of either electrode pair is indicative of the conductivity of the sample. Consequently, the current of either the first or second drive circuit is sampled to determine the conductivity of the fluid. Also included in the sensor are isolation capacitors which serve, if at all, to prevent direct common mode currents from distorting the conductivity measurement. However, these isolation capacitors do not prevent alternating common mode currents that are produced, for example, by power lines. Consequently, alternating common mode currents will still distort the conductivity measurements produced by this sensor.

SUMMARY OF THE INVENTION

The present invention includes a complementary cell having a passageway that is symmetrically disposed about the longitudinal axis of the cell and contains the fluid on which a measurement is to be made. Disposed between the passageway and the exterior of the cell are first and second sensors, which are also symmetrically disposed relative to the longitudinal axis of the cell. Due to the symmetrical or complementary nature of the cell, there exists a ground at the axis of symmetry of the cell. Consequently, the first measurement signal, generated by the first sensor, is representative of the physical phenomena existing between the axis of symmetry, or ground, and the first sensor. Likewise, the second measurement signal, generated by the second sensor, is indicative of the physical phenomena existing between the axis of symmetry and the second sensor. Furthermore, if a ground loop current or voltage is present, it can be simulated by a voltage or current source located at the ground or axis of symmetry. As previously mentioned, the ground loop current or voltage will have an effect upon the measurement. In the present invention, the ground loop current or voltage will affect both the first and second measurement signals. Consequently, there will be a distorted first measurement signal having a first measurement signal component and a first common mode voltage component, and a distorted second measurement signal having a second measurement signal component and a second common mode voltage component. Also included in the present invention is a first complementary amplifier for amplifying the distorted first measurement signal by an amount of G1. Likewise, there is a second complementary amplifier for amplifying the second measurement signal. However, the gain of the second complementary amplifier, $-G2$, is of opposite polarity relative to the gain of the first complementary amplifier. The polarity of the components of the distorted first and second signals after amplification are such that addition of the signals could cancel the common mode current components and sum the undistorted first and second measurement signals. Consequently, an adjustable summation means is provided to sum the amplified and distorted signals thereby producing a clean measurement signal. An adjustable summation means is necessary to compensate for differences in components values used in producing the first and second measurement signals.

In a preferred embodiment of the invention, a complementary conductivity sensor is provided for measuring the conductivity of a fluid. Included in the complementary conductivity sensor is a conductivity cell having a passageway symmetrically disposed about the longitudinal axis of the cell and used to contain the fluid whose conductivity is to be measured. Intermediate the exterior of the conductivity cell and the passageway are a first and second pair of electrodes which are also symmetrically disposed about the axis of symmetry of the cell. One electrode of the each pair of electrodes provides feedback to a drive circuit that maintains the fluid located near the second electrode of the pair at a defined potential. Consequently, there are first and second drive circuits. The first drive circuit maintains the fluid located near the first pair of electrodes at a voltage of V, generally an alternating voltage to prevent polarization of the electrodes. The second drive circuit, on the other hand, maintains the fluid located near the second pair of electrodes at a voltage of −V. Consequently, there is a ground located at the axis of symmetry of the conductivity cell. Furthermore, the ground defines the path through which any common mode current will enter the sensor circuitry. The current necessary to maintain the voltage V in the fluid located near the first pair of electrodes, absent any common mode current, is indicative of the conductivity of the fluid located between the axis of symmetry, or ground, and the location of the first pair of electrodes. Likewise, the current necessary to maintain the voltage −V in the fluid located near the second pair of electrodes, absent any common mode current, is representative of the conductivity of the fluid located between the axis of symmetry, or ground, and the location of the second pair of electrodes. These two signals are the first and second conductivity signals. There are also first and second sampling means for sampling and amplifying the first and second conductivity signals. If, however, there is a common mode current present, it will enter the sensor at the ground and alter the magnitudes of the currents being sampled thereby distorting the conductivity measurement. Consequently, there is distorted first conductivity signal having a first conductivity signal component and a first common mode signal component. Likewise, there is a distorted second conductivity signal having a second conductivity signal component and a second common mode signal component. However, due to the complementary nature of the circuit, the second common mode signal component is of an opposite polarity than the first common mode signal component. Consequently, by adding the first and second distorted conductivity signals the common mode current components can be cancelled. A potentiometer is used to add the first and second distorted conductivity signals, thereby cancelling the common mode current components and producing a clean conductivity signal. The potentiometer also provides a means for compensating for variations in component values between the circuits producing the first and second signals.

DETAILED DESCRIPTION

Figure 1:
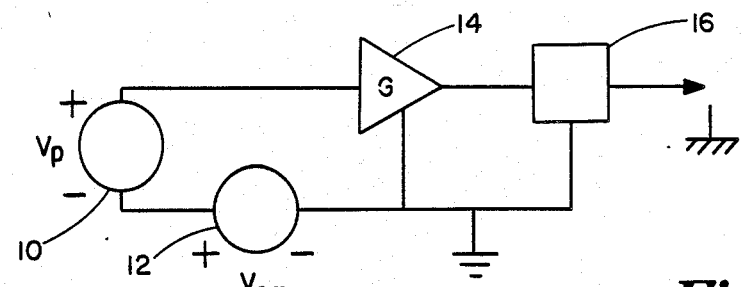
FIG. 1 is illustrative of a prior art sensor that outputs a measurement signal which is distorted by the presence of a common mode voltage.

With reference to FIG. 1, a prior art measurement device is described to emphasize the effect of common mode voltages and/or currents on measurement signals. The typical sensor detects some physical phenomena, such as temperature or pressure, and generates a signal representative of the phenomena. Consequently, the sensor and the signal representative of the sensed phenomena can be modeled by voltage source 10 that outputs a signal $V_p$. The common mode voltage is represented by common mode voltage source 12 which outputs a signal of magnitude $V_{cm}$. Due to the presence of the common mode voltage source 12, the signal input to amplifier 14 is not simply the signal representative of the sensed phenomena, $V_p$, but rather the sum of the signal representative of the sensed phenomena and the common mode voltage, $V_p$ and $V_{cm}$. Consequently, the signal output by amplifier 14 and conditioned by signal processor 16 is not representative of the sensed phenomena.

Figure 2:
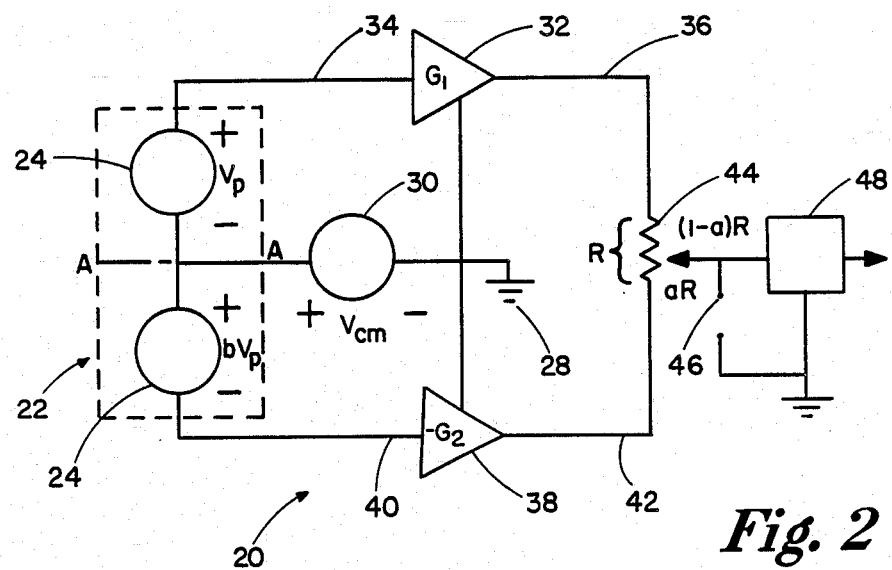
FIG. 2 illustrates the concept of a general complementary measurement device.

The complementary measurement device 20 illustrated in FIG. 2 reduces common mode voltages and currents, thereby yielding an improved measurement signal. Included in the complementary measurement device 20 is a complementary measurement cell 22 for holding the fluid to be measured. The complementary measurement cell 22 is substantially symmetrical about axis A—A. Also included in complementary measurement cell 22, and substantially symmetrically disposed about axis A—A, are a first sensor, modeled by first voltage source 24, and a second sensor, modeled by second voltage source 26. Due to the symmetry of the cell and the sensors, a ground 28 can be modeled at axis A—A. Consequently, the magnitude $V_p$ of the signal being output by the first voltage source 24 is representative of, for example, the conductivity of the fluid residing between the axis A—A and the first sensor. Likewise, the magnitude $bV_p$ of the signal being output by the second voltage source 26 is representative of, for example, the conductivity of the the of the fluid residing between axis A—A and the second sensor multiplied by the scalar b which accounts for any lack of symmetry between the two sensors.

Common mode voltages by definition exist in the ground path. Therefore, a common mode voltage source 30 outputting a signal of magnitude $V_{cm}$ models any common mode voltage existing in the ground path.

Complementary measurement device 20 also includes first amplifier 32 for amplifying the signal existing at its input 34 by an amount of G1. The signal existing at the input 34 is the sum of the voltages existing between the input 34 and ground 28. Consequently, the output signal $V_1$ existing at the output 36 of the first amplifier 32 can be represented by the following equation:

$$V_1 = G1\,(V_p + V_{cm}) \qquad (1)$$

Similarly, a second amplifier 38 is included in the complementary measurement device 20 for amplifying the signal existing at its input 40 by an amount −G2. The signal existing at the input 40 is the sum of the voltages existing between input 40 and ground 28. Consequently, the output signal $V_2$ existing at the output 42 of the second amplifier 38 can be represented by the following equation:

$$V_2 = -G2(-bV_p + V_{cm}) \quad (2)$$
$$= G2(bV_p - V_{cm})$$

A comparison of equations (1) and (2) reveals that the $V_{cm}$ terms are of opposite polarity.

A potentiometer 44 having a full range resistance of R is included in complementary measurement device 20 to sum signals $V_1$ and $V_2$. The output signal $V_o$ existing at the wiper arm 46 of potentiometer 44 can be represented by the following equation:

$$V_o = aV_1 + (1-a)V_2 \quad (3)$$

Substitution of equations (1) and (2) into equation (3), reveals the following equation:

$$V_o = V_p(aG1 + b(1-a)G2) + V_{cm}(aG1 - (1-a)G2) \quad (4)$$

If the wiper arm 46 of potentiometer 44 is adjusted according to the following equation, the common voltage term $V_{cm}$ can be eliminated:

$$aG1 = (1-a)G2 \quad (5)$$

Consequently, the output signal $V_o$ reduces to the following equation which is independent of any common mode voltage component:

$$V_o = V_p aG1(1+b) \quad (6)$$

The output signal $V_o$ can then be input to signal conditioner 48 which may, for example, digitize the signal for further transmission.

Figure 3:
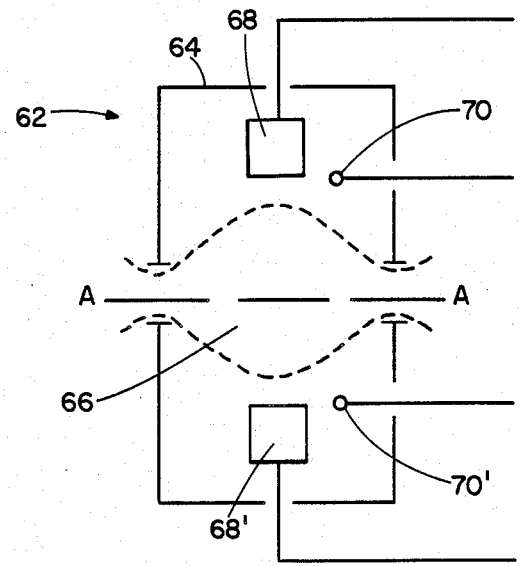
FIG. 3 is a cross section of the conductivity cell used in a preferred embodiment of the invention, the complementary conductivity measurement device.
Figure 4:
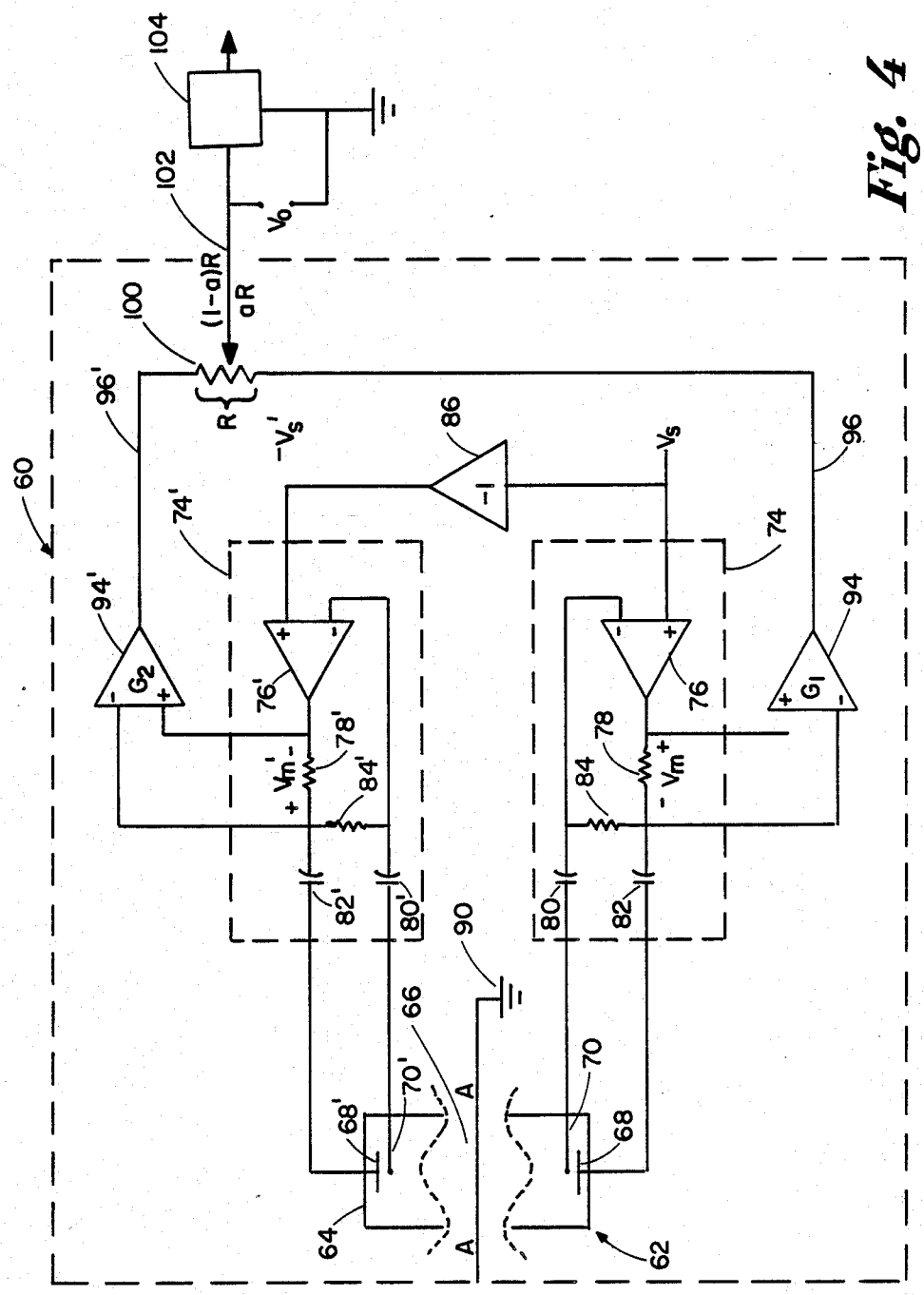
FIG. 4 illustrates the complementary conductivity measurement device, a preferred embodiment of the invention.

A preferred embodiment of the invention is the complementary conductivity measurement device 60, illustrated in FIGS. 3 and 4. Included in the complementary conductivity measurement device 60 is a substantially, and preferably, cylindrically shaped conductivity cell 62 made of a non-conductive material. The exterior surface 64 is symmetrically disposed about axis A—A. A passageway 66, also symmetrically about axis A—A, for holding the fluid whose conductivity is being measured is defined within the interior of the conductivity cell 62. A first pair of electrodes 68, 70 and a substantially similar, second pair of electrodes 68', 70' are located symmetrically about axis A—A and intermediate exterior surface 64 and passageway 66. Electrodes 70 and 70' provide feedback to drive circuits which maintain the fluid in the region of electrodes 68 and 68', respectively, at defined potentials. The conductivity cell 62 described thus far is merely exemplary. Other conductivity cells satisfying the symmetry criteria are within the scope of the present invention.

Complementary conductivity measurement device 60 includes a first complementary drive circuit 74 for maintaining a defined potential or voltage in the solution at electrode 68. First complementary drive circuit 74 includes an operational amplifier 76 whose non-inverting input is connected to a voltage source that outputs a drive signal V which is, preferably, an alternating signal to prevent polarization of the electrodes 68, 70. Electrode 70 is connected to the inverting input of operational amplifier 76 to provide a feedback signal. The output of operational amplifier 76 is essentially connected to electrode 68. The complementary drive circuit described thus far serves to maintain the fluid located near electrode 68 at the input voltage V of the operational amplifier 76, and is well-known in the art as a voltage follower circuit. First complementary drive circuit 74 also includes sampling resistor 78, located between the output of operational amplifier 76 and the electrode 68, for sampling the magnitude of the current being output by operational amplifier 76. The magnitude of the current being output by operational amplifier 76 and flowing through sampling resistor 56 is indicative of the conductivity of the fluid residing between axis A—A and electrode 68. For example, if the conductivity of the fluid being sampled is extremely low, then operational amplifier 76 would have to produce a relatively small current at its output to maintain the voltage V at electrode 68. The magnitude of this current can be sampled by measuring the voltage $V_m$ across sampling resistor 78. The resistance of sampling resistor 78 is, preferably chosen so that the voltage drop across it is relatively small. Capacitors 80 and 82, which are disposed between electrode 70 and the inverting input of operational amplifier 76, and electrode 68 and the output of operational amplifier 76, respectively, isolate electrodes 70 and 68 from direct current generated in either drive circuit 74 or from potential ground loops. Also included in the first complementary drive circuit 74 is resistor 84 to provide a dc bias current to the inverting input of operational amplifier 76.

A second complementary drive circuit 74' is provided to maintain a defined potential or voltage of $-V$ at the fluid located near electrode 68'. The components which make up the second complementary drive circuit 74' are substantially the same, and perform the same function, as the components which make up the first complementary drive circuit 74. Consequently, the components of the second complementary drive circuit 74' are given the same reference numbers as the corresponding components in the first complementary drive circuit 74 but with the addition of a prime. The second complementary drive circuit 74' differs from the first complementary drive circuit in that the non-inverting input of operational amplifier 76' is connected to a voltage source which outputs a drive signal of $-V$, the inverse of the signal driving the non-inverting input of the operational amplifier 76 in the first complementary drive circuit 74. Drive signal $-V$ can be obtained by inputting drive signal V to the inverting amplifier 86 which will output the required drive signal, $-V$. Therefore, the second complementary drive circuit 52' operates to maintain a voltage of $-V$ in the fluid located near electrode 68'. Furthermore, the magnitude of the current flowing through resistor 78' is indicative of the conductivity of the fluid residing between axis A—A and electrode 68'.

Due to the complementary nature of the complementary conductivity measurement device 60, there is essentially a ground 90 at axis A—A. The complementary nature of the device is manifested by maintaining the fluid at electrode 68 at a potential of V and the fluid at electrode 68' at a potential of $-V$, the first and second complementary drive circuits 74 and 74' and the symmetry of conductivity cell 64.

A first sampling amplifier 94 is provided to sample the magnitude of the current being output by operational amplifier 76 to maintain the fluid at electrode 68 at a potential of V. The magnitude of the current being output by operational amplifier 76, as previously mentioned, is proportional to the conductivity of the fluid residing between axis A—A and electrode 68. The magnitude of the current being output by operational amplifier is sampled by inputting the voltage $V_m$ across sampling resistor 78 to first sampling amplifier 94. The first sampling amplifier 94 amplifies the voltage signal $V_m$ by a factor of G1 and outputs a first conductivity signal on lead 96.

A second sampling amplifier 94' is provided to sample the magnitude of the current being output by operational amplifier 76' to maintain the fluid at electrode 68' at a potential of $-V$. The second sampling amplifier 94' functions in all respects like the first sampling amplifier 94 except that second sampling amplifier 74' has a gain of G2. Consequently, second sampling amplifier 94' outputs a second conductivity signal on lead 96', indicative of the magnitude of the current flowing through resistor 78'.

Complementary conductivity measurement device 60 includes potentiometer 100 for adding the first conductivity signal to the second conductivity signal. If a common mode voltage or current is present it will manifest itself in the first and second conductivity signals. However, due to the complementary nature of the complementary conductivity measurement device 60 the common mode voltage of current component in the first conductivity signal is of an opposite polarity from the common mode voltage or current component in the second conductivity signal. Consequently, when the first and second conductivity signals are added at potentiometer 100 it is possible to cancel the common mode components thereby producing a clean conductivity signal $V_o$ at wiper arm 102 that is representative of the conductivity of the fluid sample residing in passageway 66 and between electrodes 68 and 68'. Cancellation of the common mode components is achieved by adjustment of wiper arm 102.

Method of Operation

Initially, the complementary measurement device 60 is calibrated by adjusting potentiometer 100 to minimize the effects of common mode current. Typically, calibration takes place during the manufacturing stage of the complementary measurement device 60 and involves the connection of a current source to electrodes 68 and 68' to simulate a common mode current. With the common current source in place, potentiometer 100 is adjusted to eliminate the portion of the signal produced at its output, wiper arm 102, that is a result of the common mode current. The complementary conductivity measurement device 60 is now ready for use in the field.

Exemplary of the uses made of the complementary conductivity measurement device 60 is salinity measurements, typically of water in an underground aquifer. The complementary conductivity measurement device 60 is inserted into a well or bore hole which extends into the aquifer. The complementary measurement device 60 is then used to measure the conductivity of water in the aquifer; the conductivity of the water being indicative of its salinity.

Figure 5:
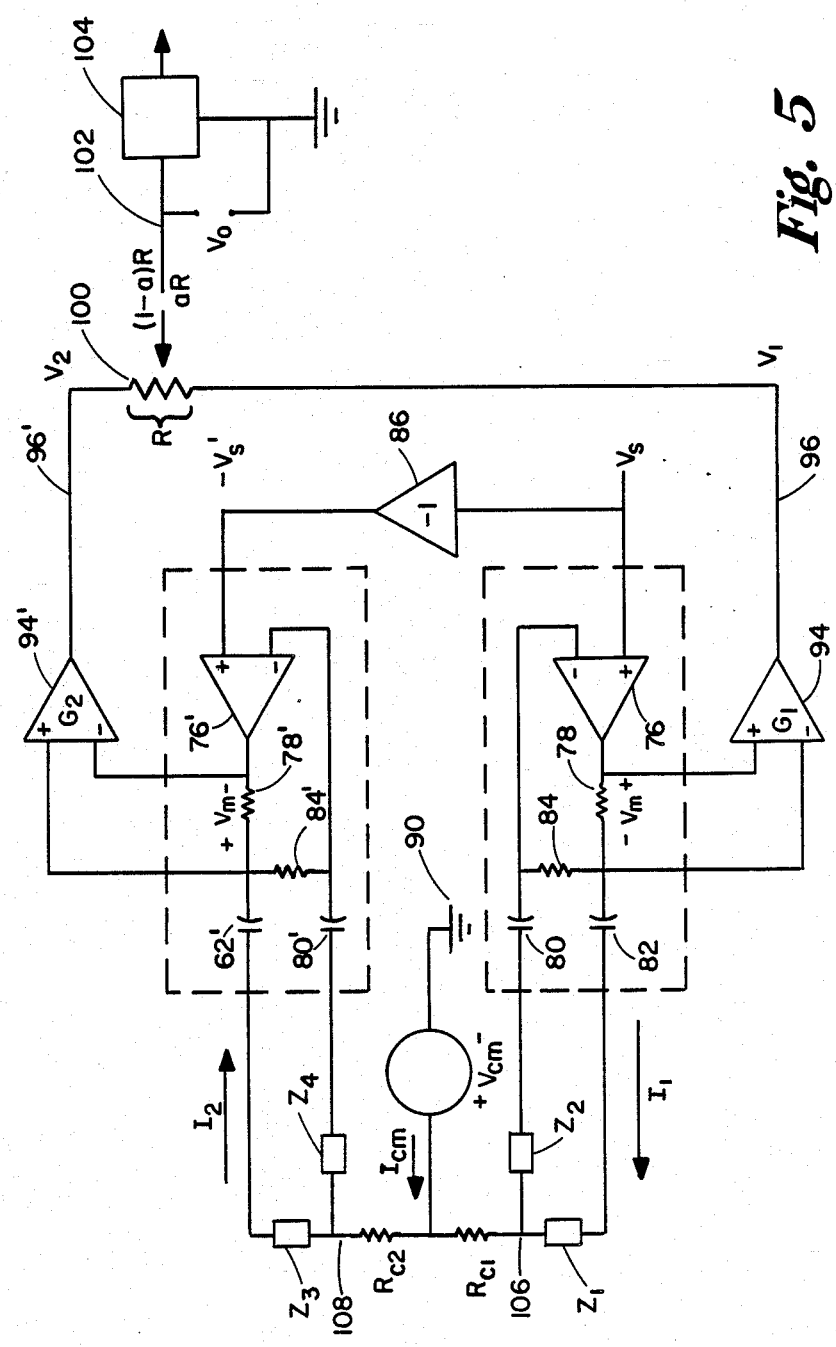
FIG. 5 illustrates the complementary conductivity measurement device with analogous electrical components representing the conductivity cell, a common mode voltage and the conductivity of the fluid being sampled.

With reference to FIG. 5, the manner in which the complementary conductivity device 60 reduces the effects of common mode currents and voltages will be described. Resistor $R_{c1}$ models the resistivity, which is the inverse of conductivity, of the fluid sample residing between axis A—A and electrode 68. Likewise, resistor $R_{c2}$ models the resistivity of the fluid sample residing between axis A—A and electrode 68'. Voltage source $V_{cm}$ models a common mode voltage which by definition is located in the ground path. Common mode voltage source $V_{cm}$ is outputting common mode current $I_{cm}$. Elements $Z_1$ and $Z_3$ are complex impedances which effectively model electrodes 68 and 68', respectively, and any build up of deposits on the electrodes. Likewise, elements $Z_2$ and $Z_4$ are complex impedances that model electrodes 70 and 70', respectively, and any deposition on the electrodes. Locations 106 and 108 represent, essentially, the points on interface between the conductivity cell 62 and the passageway 64 which are maintained at potentials $V_s$ and $-V_s'$, respectively. For purposes of this example, location 106 is maintained at a potential of $-V_s'$. Due to the high input impedances of the inverting inputs of operational amplifiers 76 and 76', the feedback paths defined by complex impedance $Z_2$ and capacitor 80, and complex impedance $Z_4$ and capacitor 80' can be considered short circuits for purposes of this analysis. Consequently, the feedback paths are directly connected to locations 106 and 108 and operational amplifiers 76, 76' will operate to maintain location 106, 108 at potentials of $V_s$ and $-V_s'$, respectively. Furthermore, since an alternating excitation voltage is being utilized, capacitors 82 and 82' can be considered short circuits. Currents $I_1$ and $I_2$ can be described by the following equations:

$$I_1 = (V_s - V_{cm})/R_{c1} \tag{7}$$

$$I_2 = (V_s' + V_{cm})/R_{c2} \tag{8}$$

Currents $I_1$ and $I_2$, absent any common mode voltage or current, are indicative of the conductivity of the fluid in conductivity cell 62. However, as equations (7) and (8) reveal currents $I_1$ and $I_2$ are now distorted by the presence of a common mode voltage, $V_{cm}$. But, due to the complementary nature of the complementary conductivity measurement device 60 the common mode voltage $V_{cm}$ term in $I_1$ is of an opposite polarity from the like term in $I_2$. Proceeding through the circuitry, the voltages across sampling resistors 78 and 78' are:

$$\begin{aligned} V_m &= I_1 R_s \\ &= (V_s - V_{cm}) R_s / R_{c1} \end{aligned} \tag{9}$$

$$\begin{aligned} V_m' &= I_2 R_s' \\ &= (V_s' + V_{cm}) R_s' / R_{c2} \end{aligned} \tag{10}$$

where $R_s$ and $R_s'$ denote resistors 78 and 78', respectively. The voltage $V_{cm}$ across sample resistor 78 is input to amplifier 94 which outputs a signal $V_1$, on lead 96, represented by the following equation:

$$\begin{aligned} V_1 &= G_1 V_m \\ &= G_1(V_s - V_{cm}) R_s / R_{c1} \end{aligned} \tag{11}$$

Likewise, the signal output by amplifier 94' on lead 96' can be represented by the following equation:

$$\begin{aligned} V_2 &= G_2 V_m' \\ &= G_2(V_s' + V_{cm}) R_s' / R_{c2} \end{aligned} \tag{12}$$

Signals $V_1$ and $V_2$, both of which contain oppositely signed common mode voltage $V_{cm}$ terms, are then summed by potentionmeter 100. The sum or output signal $V_o$ at wiper arm 102 of potentiometer 100 can be represented by the following equation:

$$V_0 = aV_1 + (1-a)V_2 \qquad (13)$$
$$= aG_1V_sR_s/R_{c1} + (1-a)G_2V_s'R_s'/R_{c2} +$$
$$V_{cm}((1-a)G_2R_s'/R_{c2} - aG_1R_s/R_{c1})$$

Let $$G_2V_s'R_s'/R_{c2} = bG_1V_sR_s/R_{c1} \qquad (14)$$

where be represents any lack of symmetry. Substitution of equation (14) into equation (13) reveals that the summation of signals $V_1$ and $V_2$ by potentionmeter 100 produces the following equation:

$$V_o = (G_1V_sR_s/R_{c1})(a+b(1-a)) + (V_{cm}G_1R_s/R_{c1})(b(1-a)-a) \qquad (15)$$

If potentiometer 100 is adjusted such that $$b(1-a) = a \qquad (16)$$

then the common mode voltage $V_{cm}$ term drops out of the signal representing the output signal $V_o$. Consequently, the equation representing output signal $V_o$ reduces to the following equation:

$$V_o = 2aG_1V_sR_s(1/R_{c1}) \qquad (17)$$

which is independent of any common mode current or voltage term. Analysis of equation (17) reveals that the output signal $V_o$ is equivalent to the conductance $(1/R_{c1})$ of the fluid residing in passageway 66 multiplied by a scalar $(2aG_1V_sR_s)$. Consequently, the complementary conductivity measurement device 60 produces a conductivity signal that is virtually undistorted by common mode voltages or currents.

What is claimed is:

1. A measurement apparatus for reducing common mode effects, comprising:
   first means and second means symmetrically located relative to a sample voltage of fluid for sensing a parameter associated with the sample volume, said first and second means having respective first and second impedances;
   third means communicating with said first means for generating a first common mode signal;
   fourth means communicating with said second means for generating a second common mode signal; and
   fifth means for combining said first and second common mode signals for reducing common mode effects.

2. An apparatus, as claimed in claim 1, wherein:
   said third means generates a first measurement signal relating to the parameter being sensed and said fourth means generates a second measurement signal relating to the parameter being sensed.

3. An apparatus, as claimed in claim 2, wherein:
   said fifth means is responsive to said first and second measurement signals and combines them to produce a combined signal representative of the parameter being sensed.

4. An apparatus, as claimed in claim 3, wherein:
   said fifth means includes means for adjusting the signal outputted by said fifth means.

5. An apparatus, as claimed in claim 4, wherein: said means for adjusting includes a potentiometer.

6. An apparatus, as claimed in claim 1, wherein: said third means is complementary to said fourth means wherein a first measurement signal outputted by said third means is substantially equal in magnitude to a second measurement signal outputted by said fourth means, said first and second measurement signals relating to the parameter.

7. An apparatus, as claimed in claim 1, wherein:
   said third means includes first voltage follower circuit means.

8. An apparatus, as claimed in claim 7, wherein:
   said fourth means includes second voltage follower circuit means.

9. A measurement apparatus for reducing common mode effects, comprising:
   first means for sensing a parameter;
   second means communicating with said first means for generating a first common mode signal, said second means including first sampling resistor means;
   third means for generating a second common mode signal; and
   fourth means for combining said first and second common mode signals for reducing common mode effects.

10. An apparatus, as claimed in claim 9, wherein: said second means includes sampling resistor means.

11. An apparatus, as claimed in claim 1, wherein:
    said third means includes first amplifying means, the output of which communicates with said fifth means.

12. An apparatus, as claimed in claim 11, wherein:
    said fourth means includes second amplifying means, the output of which communicates with said fifth means.

13. A measurement apparatus for reducing common mode effects, comprising:
    first means for sensing a parameter, said first means including a passageway for containing fluid having the parameter to be measured and having an axis of symmetry, said passageway being defined by a first side and a second side with each of said first and second sides being spaced an equal distance from said axis of symmetry;
    second means communicating with said first means for generating a first common mode signal;
    third means for generating a second common mode signal; and
    fourth means for combining said first and second common mode signals for reducing common mode effects.

14. A measurement apparatus for reducing common mode effects, comprising:
    first means for sensing a parameter, said first means including a passageway for containing fluid having the parameter to be measured, a first pair of electrodes and a second pair of electrodes, wherein said first pair of electrodes and said second pair of electrodes are located symmetrically relative to said passgeway;
    second means communicating with said first means for generating a first common mode signal;
    third means for generating a second common mode signal; and
    fourth means for combining said first and second common mode signals for reducing common mode effects.

15. An apparatus, as claimed in claim 14, wherein:

a first electrode of each of said first and second pairs of electrodes is maintained at a predetermined potential.

16. An apparatus, as claimed in claim 15, wherein:
a second electrode of each of said first and second pairs of electrodes is disposed in a feedback path for use in maintaining the fluid near said second electrodes of said first and second pairs of electrodes at said predetermined potentials.

17. A complementary conductivity measurement apparatus for reducing common mode effects, comprising:
conductivity cell means disposed in a fluid whose conductivity is to be measured, said conductivity means including a passageway and first and second pairs of electrodes, said first and second pairs of electrodes being symmetrically disposed relative to said passageway wherein said passageway has an axis of symmetry and the potential about said axis of symmetry is substantially equal to zero, said first pair of electrodes including a first electrode and a second electrode and said second pair of electrodes including a first electrode and a second electrode;
first complementary measurement means communicating with said conductivity cell means, said first complementary measurement means including voltage follower circuit means, sampling resistor means and amplifying means, the output of said voltage follower circuit means communicating with said first electrode of said first pair of electrodes, said second electrode of said first pair of electrodes providing an input to said voltage follower circuit means, said sampling resistor means being responsive to said output of said voltage follower circuit means and providing an input to said amplifying means, said voltage follower circuit means for use in maintaining the fluid near said second electrode of said first pair of electrodes at a predetermined potential;
second complementary measurement means communicating with said cell conductivity means, said second complementary measurement means including voltage follower circuit means, sampling resistor means and amplifying means, the output of said voltage follower circuit means communicating with said first electrode of said second pair of electrodes, said second electrode of said second pair of electrodes providing an input to said voltage follower circuit means, said sampling resistor means being responsive to said output of said voltage follower circuit means and providing an input to said amplifying means, said voltage follower circuit means for use in maintaining the fluid near said second electrode of said first pair of electrodes at a predetermined potential; and
means for combining outputs from said amplifying means of said first complementary measurement means and said amplifying means of said second complementary measurement means wherein said means for combining outputs a signal relating to the magnitude of the parameter being measured while reducing common mode effects.

18. A method for reducing common mode effects while measuring a desired parameter, comprising:
generating a first measurement signal component relating to the parameter being measured;
generating a second measurement signal component relating to the parameter being measured;
providing first means and second means symmetrically located relative to a sample volume of fluid for sensing a parameter associated with the sample volume, said first and second means having respective first and second impedances;
producing a first common mode signal component using said first sensing means;
producing a second common mode signal component using said second sensing means; and
processing said first and second measurement signal components using processing means to provide a magnitude relating to the parameter being measured while reducing common mode effects represented by said first common mode signal component and said second common mode signal component.

19. A method, as claimed in claim 18, wherein:
said step of producing said second common mode signal component includes producing said second common mode signal component having a magnitude substantially equal that, and polarity substantially opposite that of said first common mode signal component.

20. A method
for reducing common mode effects while measuring a desired parameter, comprising:
generating a first measurement signal component relating to the parameter being measured;
generating a second measurement signal component relating to the parameter being measured;
providing a first pair of electrodes and
a second pair of electrodes;
producing a first common mode signal component using said first pair of electrodes;
producing a second common mode signal component using said second pair of electrodes; and
processing said first and second measurement signal components using processing means to provide a magnitude relating to the parameter being measured while reducing common mode effects represented by said first common mode signal component and said second common mode signal component.

21. A method, as claimed in claim 20, wherein:
said step of generating said first measurement signal component includes driving a first electrode of said first pair of electrodes and receiving feedback from a second electrode of said first pair of electrodes.

22. A method, as claimed in claim 21, wherein:
said step of generating said first measurement signal component includes amplifying a signal obtained using said first electrode.

23. A method
for reducing common mode effects while measuring a desired parameter, comprising:
providing conductivity cell means having a passageway for containing a sample of a fluid whose conductivity is to be measured;
symmetrically disposing first and second pairs of electrodes about said passageway;
generating a first measurement signal component relating to the parameter being measured;
generating a second measurement signal component relating to the parameter being measured;
producing a first common mode signal component using said first pair of electrodes;
producing a second common mode signal component using said second pair of electrodes; and processing said first and second measurement signal components using processing means to provide a magnitude relating to the parameter being measured while reducing common mode effects represented by said first common mode signal component and said second common mode signal component.

24. A method for reducing common mode effects while measuring a desired parameter, comprising:

generating a first measurement signal component relating to the parameter being measured;

generating a second measurement signal component relating to the parameter being measured;

producing a first common mode signal component using said first pair of electrodes;

producing a second common mode signal component using said second pair of electrodes;

processing said first and second measurement signal components using processing means to provide a magnitude relating to the parameter being measured while reducing common mode effects represented by said first common mode signal component and said second common mode signal component; and calibrating said processing means at least once before measuring the desired parameter.

* * * * *